United States Patent
Kottayil et al.

(10) Patent No.: US 10,406,122 B2
(45) Date of Patent: *Sep. 10, 2019

(54) INTRAVENOUS ADMINISTRATION OF TRAMADOL

(71) Applicant: Revogenex Ireland Ltd., Dublin (IE)

(72) Inventors: S. George Kottayil, West Windsor, NJ (US); Jeffrey H. Ping, Suwanee, GA (US)

(73) Assignee: Revogenex Ireland Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,684

(22) Filed: May 7, 2018

(65) Prior Publication Data

US 2018/0303771 A1    Oct. 25, 2018

Related U.S. Application Data

(63) Continuation of application No. 15/407,133, filed on Jan. 16, 2017, now Pat. No. 9,962,343, which is a continuation of application No. 14/550,279, filed on Nov. 21, 2014, now Pat. No. 9,561,195, which is a continuation of application No. 13/445,526, filed on Apr. 12, 2012, now Pat. No. 8,895,622.

(60) Provisional application No. 61/553,609, filed on Oct. 31, 2011, provisional application No. 61/474,345, filed on Apr. 12, 2011.

(51) Int. Cl.
| | |
|---|---|
| *A61K 31/135* | (2006.01) |
| *A61K 31/485* | (2006.01) |
| *A61K 31/00* | (2006.01) |
| *A61K 9/00* | (2006.01) |
| *A61K 31/138* | (2006.01) |
| *A61K 45/06* | (2006.01) |

(52) U.S. Cl.
CPC .......... *A61K 31/135* (2013.01); *A61K 9/0019* (2013.01); *A61K 31/138* (2013.01); *A61K 31/485* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 8,895,622 | B2* | 11/2014 | Kottayil | ............... A61K 31/485 |
| 9,561,195 | B2* | 2/2017 | Kottayil | ............... A61K 31/485 |
| 9,566,253 | B2* | 2/2017 | Kottayil | ............... A61K 31/485 |
| 9,962,343 | B2* | 5/2018 | Kottayil | ............... A61K 31/485 |

OTHER PUBLICATIONS

Tramal® Data Sheet, Aug. 2008, published online by medsafe.govt.nz, downloaded on Feb. 4, 2014 from "https://web.archive.org/web/20111018060034/http://www.medsafe.govt.nz/profs/Datasheet/t/TramalcapSRtabinjoraldrops.pdf", 12 pages.*
Chrubasik et al., European Journal of Anaesthesiology, 1992, vol. 9, pp. 23-28.*
Webb et al., Anesthesia & Analgesia, 2002, vol. 95, pp. 1713-1718.*
Alhashemi et al., Canadian Journal of Anesthesia, 2004, vol. 51(4), pp. 342-347.*
Gramke et al., Anesth Analg, 2006, vol. 102, pp. 755-758.*
Stiller et al., Acta Anaesthesiologica Scandinavica, 2007, vol. 51, pp. 322-330.*

* cited by examiner

*Primary Examiner* — Savitha M Rao
*Assistant Examiner* — Gregg Polansky
(74) *Attorney, Agent, or Firm* — Davidson, Davidson & Kappel, LLC

(57) ABSTRACT

A method of treating pain, e.g., acute post-operative pain, by administering to a human patient(s) a therapeutically effective dose of tramadol intravenously over a prolonged time period is disclosed. In certain embodiments, the dose is intravenously administered in a time period from about 10 minutes to about 3 hours, preferably from about 10 minutes to about 30 minutes. In other embodiments, intravenous doses are administered at suitable time intervals over a time period from about 3 hours to 48 hours.

23 Claims, 2 Drawing Sheets

INTRAVENOUS ADMINISTRATION OF TRAMADOL

This application is a continuation of U.S. patent application Ser. No. 15/407,133, filed on Jan. 16, 2017, which is a continuation application of U.S. patent application Ser. No. 14/550,279 filed on Nov. 21, 2014, which is a continuation application of U.S. patent application Ser. No. 13/445,526, filed on Apr. 12, 2014 which claims priority of U.S. Patent Application Ser. No. 61/553,609, filed on Oct. 31, 2011, and U.S. Patent Application Ser. No. 61/474,345, filed on Apr. 12, 2011; the disclosures of which are all hereby incorporated by reference herein in their entirety.

BACKGROUND OF THE INVENTION

Tramadol is a centrally acting synthetic analgesic with a dual mechanism of action attributed to the racemic form of the drug, comprised of µ-opioid activity (binding to µ-opioid receptors and monoamine (serotonin and noradrenalin) reuptake inhibition. Tramadol is an analog of the phenanthrene group of opium alkaloids, which includes morphine and codeine, and is structurally related to these opioids (Grond S and Slabotzi A. Clinical pharmacology of tramadol. Clin Pharmacokinet. 2004; 43:879-923). Like codeine, there is a substitution of the methyl group on the phenol ring that imparts a relatively weak affinity for opioid receptors. (+)-Tramadol is a more potent inhibitor of serotonin uptake, while (−)-tramadol is a more potent inhibitor of norepinephrine uptake. The opioid-like activity of tramadol derives from low affinity binding of the parent compound to µ-opioid receptors and higher affinity binding of its main metabolite. Tramadol affinity to µ opioid receptors is about 10 times weaker than codeine, 60 times weaker than dextropropoxyphene and 6,000 times weaker than morphine. The active metabolite O-desmethyltramadol (M1) possesses a higher affinity to the µ opioid receptor than tramadol and displays analgesic activity (Leppert W, 2009).

Tramadol was originally developed by the German pharmaceutical company Grünenthal GmbH in the late 1970s and is marketed globally under the trade names TRAMAL® and others outside of the United States. The approved doses of tramadol are 50 mg or 100 mg administered as a slow injection every 4-6 hours (Tramadol Core Product Label, 2008). In the U.S., tramadol is approved by the Food and Drug Administration (FDA) and marketed as an oral capsule/tablet for moderate to moderately severe pain in adults. Tramadol was first approved in the US in April 1995 under the trade name, ULTRAM® (Ortho-McNeil-Janssen Pharmaceuticals, Inc). Tramadol is also an active agent in an extended release product, Ultram® ER, and a combination product with acetaminophen, ULTRACET®. In the US, tramadol is only available as immediate release tablets or extended release tablets. Other tramadol formulations approved in several countries include tablets, capsules, effervescent powders, and suppositories (Grond and Sablotzki, 2004; Rosenberg, 2009). The approved intravenous regimen in India is an initial injection of 50 mg infusion over 2-3 min, followed by 50 mg every 10-20 minutes if necessary up to 250 mg for the first hour. Maintenance doses are 50-100 mg every 4-6 hours with a maximum dose of 600 mg daily (Tramadol, CIMS Data_India).

Postoperative pain management with tramadol has effectively utilized a variety of delivery methods, including bolus injection (IV or IM), continuous infusions and patient controlled analgesia (PCA) pumps, and various combinations of these methods (Scott and Perry, 2000; Grond and Sablotzki, 2004). The potency ratio of IV tramadol to IV morphine is approximately 1:10, while the ratio for IV fentanyl is 1:979 (Grond and Sablotzki, 2004).

The "on-demand" analgesic efficacy of tramadol was compared to morphine in the 24-hour post-operative period for 523 patients undergoing abdominal surgery (Vickers M D, Paravicini D. Comparison of tramadol with morphine for post-operative pain following abdominal surgery. Eur J Anesthesiol. 1995; 12: 265-71). Patients who reported postoperative pain received an initial dose (either tramadol 100 mg or morphine 5 mg i.v.) and, if necessary, repeat i.v. or i.m. doses of tramadol 50 mg or morphine 5 mg on demand over the first 90 minutes. Further doses up to a total of 400 mg tramadol or 40 mg morphine could then be given after 90 minutes up to 24 hours after the first dose of study medication. The primary efficacy parameter was the responder rate (no or slight pain) within the first 90 minutes of treatment. Responder rates were 72.6% for tramadol and 81.2% for morphine, which were statistically equivalent and within the predefined range of ±10%. Mean cumulative doses were 188.2 mg for the first 90 minutes and 157.1 mg for the subsequent 22.5 hours in the tramadol group and 13.9 mg and 18.4 mg, respectively in the morphine group. The main adverse events were gastrointestinal in both groups, with mild nausea, dry mouth, vomiting, dyspepsia and hiccups reported most frequently.

The analgesic effect of continuous infusion of tramadol was compared to repeated bolus administration in 135 patients undergoing abdominal surgery (Rud U, Fischer M V, Mewes R, Paravcini D., "Postoperative Analgesie mit Tramadol Kontinuierliche Infusion versus repetitive" (Postoperative analgesia with tramadol. Continuous infusion versus repetitive bolus administration), Bolusgabe Anaesthesist. 1994; 43:316-321. (German)). Patients were randomized at the time of the first request for pain treatment. All patients received a loading dose of tramadol 100 mg i.v. Subsequent treatment was administered in a double-blind manner; patients in the infusion group were given a continuous infusion of tramadol 12 mg/h for 24 hours, whereas patients in the bolus group received placebo infusion. In both groups, additional bolus doses of tramadol 50 mg i.v. were given as required. Pain relief was monitored by means of a visual analog scale (VAS) up to 6 hours after surgery. The number of additional boluses and the amount of tramadol administered at 6 hours and 24 hours was also used to assess analgesic efficacy. More patients in the infusion group assessed their pain relief as excellent or good compared to the bolus group (76.5% vs 65.6%). Only a few patients complained of insufficient analgesia, with more patients in the bolus group reporting inadequate pain relief than in the infusion group (7.5% vs 4.4%). A higher percentage of patients in the bolus group required two or more boluses compared to the infusion group (59.7% vs 30.8%). After 6 hours, the average tramadol consumption was 223.5±53.7 mg in the infusion group and 176.6±63.1 mg in the bolus group (p≤0.05). After 24 hours, tramadol consumption was 449.5±66.0 mg and 201.6±83.9 mg (p≤0.001), respectively. Adverse events were reported by 25% of patients in both groups, with no significant differences and no patient terminated the trial for an adverse event. There were no significant effects on blood pressure or heart rate. The authors concluded that continuous infusion was more effective in the first 6 hours after surgery. However, excess consumption by the infusion group was statistically greater than the bolus group at both 6 hours and 24 hours post surgery.

Intermittent bolus and continuous infusion of tramadol were evaluated in a postoperative study of 35 patients undergoing major abdominal gynecologic surgery (Chrubasik J, Buzina M, Schulte-Monting J, Atanassoff P, Alon E. Intravenous tramadol for post-operative pain-comparison of intermittent dose regimens with and without maintenance infusion. Eur J Anaesthesiol. 1992; 9:23-28). The study was randomized and double-blind and used tramadol infusion 15 mg/h or saline. Additional boluses of tramadol 100 mg were given as requested. The patients in the infusion group required 60% less tramadol on demand (p<0.01) and had better pain relief (p<0.05), as assessed by VAS, than the group that received the saline infusion. Total tramadol consumption, however, was about 30% higher in the infusion group (p<0.05) and was associated with and increased incidence of minor adverse events. Tramadol was ineffective as pain relief within 2 hours of the beginning of treatment in 6% of the infusion group and 20% of the bolus group. Thus, continuous infusion was preferred to "on-demand" bolus treatment.

A meta-analysis of nine randomized, controlled trials indicated that tramadol was as effective as other opioids, including morphine, for control of postoperative pain (Scott and Perry, 2000). Pain in these patients was described as moderate to severe, with initial postoperative pain reported as >60 on a 100-point visual analog scale or as moderate or severe on a 4- or 5-point verbal response scale. The first dose of analgesia was administered when patients reported moderate to severe pain in the postoperative setting. Studies that did not adequately record baseline pain severity or response to analgesia, were not randomized or controlled or contained less than 45 patients were excluded from the meta-analysis. Tramadol, administered in a dose titrated to pain response and via either IV (intravenous) or IM (intramuscular) intermittent injection, reduced pain intensity by 46.8% to 57.6% after 4 to 6 hours compared to 69.8% for morphine and 25.6% to 51.3% for pentazocine. Efficacy of tramadol was maintained for the duration of the studies, which were ≤72 hours, and was comparable to morphine or alfentanil. However, the onset of action of tramadol was slower than morphine, as assessed by measurements approximately 3 hours after the first dose. There were no significant differences in the percentage of patients treated with tramadol or morphine and who also required rescue medication. The patient global response and physician global response were similar for tramadol and for other opioids.

Tramadol injection (IV/IM/SC) is approved and used for the management of moderate to severe acute postoperative pain in several regions, including Europe, India and Australia/New Zealand (however, this dosage form is not available in the USA). Tramadol ampoules or vials for IV, IM and SC administration and preservative-free solutions for injection by the various spinal routes (epidural, intrathecal, caudal, etc.) are available forms in these regions. Tramadol formulations approved in several countries include, tablets, capsules, effervescent powders, and suppositories (Grond and Sablotzki, 2004; Rosenberg, 2009).

There is extensive data demonstrating that tramadol use is not associated with the classical opioid side effects seen with more potent opioids. There are numerous reports of the safety and efficacy of tramadol (Lee et al., 1993; Scott and Perry, 2000; Grond and Sablotzki, 2004). The most common adverse events of tramadol administration are nausea, dizziness, headache, somnolence, sweating, fatigue, constipation, dry mouth and vomiting. However, tramadol use, particularly with high doses, has been associated with seizures, and the risk of seizures is increased in the presence of drugs that reduce seizure threshold, head trauma or prior history of seizures.

Patients undergoing surgery, for example, total knee arthroplasty (TKA) and total hip arthroplasty (THA), typically demonstrate a need for short-term analgesia, which is critical for earlier mobilization and rehabilitation. In this setting, assuring adequate pain relief without providing extensive medical oversight required for some methods of treatment (such as neuraxial anesthesia) and prevention of effects such as opiate-induced respiratory depression and dependency would be highly beneficial (Sinatra et al., 2002).

The goal of post-surgical pain management is twofold: i) to provide a quick onset of analgesic or pain relief and ii) to reduce or modulate the quality and intensity of pain a patient experiences in the post-surgical period. While current treatments for management of post-surgical acute pain are useful, there is a need for improved methods for treating post-surgical acute pain.

OBJECTS AND SUMMARY OF THE INVENTION

It is an object of the present invention to provide a method of treating pain in human patients.

It is a further object of the present invention to provide a method of treating pain in human patients who are unable to take oral medications, such as in a post-operative condition.

It is a further object of the present invention to provide a method of treating pain in human patients which takes advantage of the faster onset of intravenous administration of tramadol while providing additional benefits not available via current methodologies of tramadol intravenous administration.

It is another object of the present invention to provide a method of providing a safe and effective alternative injectable analgesic for use in the acute postoperative setting.

It is another object of the present invention to provide a method for treating pain in, e.g., the acute postoperative setting which is opioid-sparing.

It is another object of the present invention to provide a method for treating pain with tramadol in human patients in a manner which reduces side-effects (such as, e.g., nausea).

It is a further object of the present invention to provide a method of treating pain with a drug and dosage regimen that provides a positive benefit-risk profile, and which addresses an unmet medical need for the management of acute postoperative pain.

In accordance with the above-mentioned objects and others, the present invention is directed in part to a method of treating pain, a method of providing effective analgesia, a method of providing effective pain management, and/or a method of treating acute pain in a human patient(s) comprising administering to a human patient(s) a therapeutically effective dose of tramadol intravenously over a time period from about 10 minutes to about 3 hours. In certain preferred embodiments, the present invention is directed in part to a method of treating pain, comprising administering to a human patient(s) a therapeutically effective dose of tramadol intravenously over a time period from about 10 minutes to about 45 minutes. In preferred embodiments, the present invention is directed in part to a method of treating pain, comprising administering to a human patient(s) a therapeutically effective dose of tramadol intravenously over a time period from about 10 minutes to about 30 minutes.

In certain preferred embodiments, the present invention is directed in part to a method of treating pain, comprising administering to a human patient(s) a therapeutically effective dose of tramadol intravenously over a time period from about 10, 11, 12, 13, 14, 15, 16, 17, 18, 19, 20 21, 22, 23, 24, 25, 26, 27, 28, 29 30, 31, 32, 33, 34, 35, 36, 37, 38, 39, 40, 41, 42, 43, 44 or 45 minutes.

In certain preferred embodiments, the method of treatment further comprises administering further therapeutically effective doses of tramadol at intervals from about 2 to about 6 hours to treat pain in the human patient(s), wherein each dose of tramadol is administered intravenously over a time period from about 10 minutes to about 45 minutes, preferably in about 15 to about 30 minutes. In certain preferred embodiments, the method further comprises administering the dose of tramadol in about 10 minutes to about 45 minutes at suitable intervals (e.g., from about 2 to about 6 hours) for at least about 48 hours, or for at least about 3, 4, 5 or 6 days, or until the patient no longer needs intravenous treatment for pain, e.g., in a hospital setting.

In certain preferred embodiments, the therapeutically effective dose of tramadol administered is from about 50 mg to about 200 mg. In certain preferred embodiments, the effective dose of tramadol administered is about 50 mg. In certain preferred embodiments, the effective dose of tramadol administered is about 70 mg. In other preferred embodiments, the effective dose of tramadol administered is about 100 mg.

Further aspects of the invention are directed to diluting the dose of tramadol in from about 50 ml to about 500 ml (and preferably from about 50 ml to about 100 ml) of a pharmaceutically acceptable fluid for injection such as normal saline, e.g., in a bag, and standardizing the administration of the injection of the dose of tramadol via the use of a pump.

In another preferred embodiment, the dose of tramadol is provided in the form of a sterile solution at a concentration of about 50 mg tramadol hydrochloride/1 ml prior to dilution.

In certain further preferred embodiments, the dose of tramadol prior to dilution is contained in one or more ampoules. In certain preferred embodiments, the ampoules contain the dose of tramadol (e.g., tramadol hydrochloride) together with a buffering agent (e.g., sodium acetate) in water for injection (e.g., about 1 ml to about 5 ml).

In certain further preferred embodiments, the method further comprises diluting the dose of tramadol into an IV bag for administration to the patient.

In certain preferred embodiments, the method further comprises administering the intravenous dose such that the Tmax for tramadol for intravenous administration over 15 (±2) minutes occurs at from about 0.186 hours to about 0.848 hours after the start of intravenous administration of the dose.

In certain preferred embodiments, the intravenous administration of tramadol in accordance with the present invention in healthy human subjects achieves a tramadol Cmax of about 541 ng/ml±126 for a 50 mg intravenous dose of tramadol hydrochloride. In certain preferred embodiments, the Tmax for tramadol for such intravenous administration over 15 (±2) minutes is about 0.375 hours±0.189 hours. In certain preferred embodiments, the $AUC_t$ for such intravenous administration is 4008±1044 ng·h/ml.

In certain preferred embodiments, the intravenous administration of tramadol in accordance with the present invention achieves a tramadol Cmax of about 1250 ng/ml±236 for a 100 mg intravenous dose of tramadol hydrochloride. In certain preferred embodiments, the Tmax for for tramadol for such intravenous administration over 15 (±2) minutes is about 0.406 hours±0.442 hours. In certain preferred embodiments, the $AUC_t$ for such intravenous administration is 11176±4266 ng·h/ml.

In certain preferred embodiments, the method further comprises administering the intravenous dose such that the Tmax for the mono-O-desmethyl-tramadol (M1) metabolite of tramadol for intravenous administration over 15 (±2) minutes occurs at from about 0.55 hours to about 2.63 hours after the start of intravenous administration of the dose.

In certain preferred embodiments, the intravenous administration of tramadol in accordance with the present invention achieves a Cmax of the desmethyl (M1) metabolite of about 78.6 ng/ml±12.4 for a 50 mg intravenous dose of tramadol hydrochloride. In certain preferred embodiments, the Tmax for the desmethyl (M1) metabolite for such intravenous administration over 15 (±2) minutes is about 1.53 hours±0.57 hours. In certain preferred embodiments, the $AUC_t$ for such intravenous administration is 1086±149 ng·h/ml.

In certain preferred embodiments, the intravenous administration of tramadol in accordance with the present invention achieves a Cmax of the desmethyl (M1) metabolite of about 165 ng/ml±48 for a 100 mg intravenous dose of tramadol hydrochloride. In certain preferred embodiments, the Tmax for the desmethyl (M1) metabolite for such intravenous administration over 15 (±2) minutes is about 1.59 hours±1.04 hours. In certain preferred embodiments, the $AUC_t$ for such intravenous administration is 2730±1040 ng·h/ml.

In certain additional preferred embodiments, the method further comprises intravenously administering an initial loading dose of tramadol comprising a dose of up to about 150 mg over the time periods set forth above, and preferably over a time period from about 10 minutes to about 30 minutes, and thereafter administering further doses of tramadol at suitable therapeutically effective time intervals, e.g., about 6 hour intervals to treat pain in said patient, wherein each dose of tramadol is administered intravenously over the time periods set forth above, and preferably over a time period from about 10 minutes to about 30 minutes.

The present invention is further directed in part to a method for treating pain in humans, comprising providing a dose of tramadol in solution at a concentration from about 25 mg/ml to about 200 mg/ml; diluting the dose of tramadol in a volume of normal saline to provide a unit dose from about 50 mg to about 200 mg, in said volume of normal saline; and administering the dose of tramadol intravenously over the time periods set forth above, and preferably over a time period from about 10 minutes to about 30 minutes. In certain embodiments, the method further comprises administering additional doses of tramadol intravenously as above at suitable therapeutically effective intervals to treat pain, e.g., from about 2 to about 6 hours, such that a daily dose of from about 200 mg to about 2 g tramadol is intravenously administered.

In certain preferred embodiments of the present invention, the method further comprises administering a first dose of tramadol to the patient intra-operatively at wound closure, or from first demand of analgesia postoperatively, and administering said further doses of intravenous tramadol for at least two days post-surgery.

In certain preferred embodiments of the present invention, the method further comprises the concomitant administration of one or more opioid analgesics, preferably via the injectable (e.g., intravenous) route as rescue medicine to the patient to treat breakthrough pain that the patient experiences, e.g., for the time period of at least about 48 hours post-surgery. Several options are available for postoperative pain management (Singelyn et al., 1998; Sinatra et al., 2002; both of which are hereby incorporated by reference). Options include intermittent "on-demand" analgesia, continuous epidural analgesia with opioids and/or local anesthetics is effective, or to provide a combination of nerve blocks with long-acting local anesthetics and/or opioids initiated intra-operatively and continued into the immediate postoperative period. For example, most Total knee Arthroplasty (TKA) or Total Hip Arthroplasty (THA) procedures are currently performed with regional (or neuraxial) or other nerve blocks and without general anesthesia. In certain preferred embodiments of the invention, the method further comprises administering a rescue opioid analgesic using Patient Controlled Analgesia (PCA). In certain preferred embodiments, the intravenous administration of opioid analgesic also or alternatively comprises opioid analgesic (e.g., morphine) intravenously to the patient at an effective dose (e.g., morphine in an amount of about 0.05 mg/kg) as a bolus at the end of surgery or upon first demand of analgesia postoperatively, to provide effective analgesia to the patient(s).

In certain preferred embodiments of the invention, the first dose of tramadol is administered on first demand of analgesia postoperatively. Thereafter, the method may further comprise administering a therapeutically (analgesically) effective dose intravenous opioid analgesic to the patient at the end of the surgery, to provide effective analgesia to the patient(s).

In certain preferred embodiments of the invention, the first dose of tramadol is administered to the patient intra-operatively at wound closure. In such embodiments, the method may further comprise administering a bolus of a therapeutically (analgesically) effective dose of intravenous opioid analgesic to the patient if the patient requests analgesia before the second dose of tramadol, to provide effective analgesia to the patient(s).

In preferred embodiments where the tramadol is administered for the treatment of post-operative pain, the treatment of pain in the patient is opioid-sparing over the first 48 hours post-surgery.

The invention is also directed in part to a method of treating pain, comprising administering to a human patient a therapeutically effective dose of tramadol intravenously over a time period from about 30 minutes to about 48 hours, preferably over a time period from about 3 hours to about 48 hours, or from about 24 hours to about 48 hours, i.e., in a much slower infusion, e.g., from about 0.05 ml to about 2 ml per minute from a pre-mixed bag containing from about 100 ml to about 3 liters containing an effective amount of tramadol, e.g., a dose from about 50 mg to about 200 mg.

In certain preferred embodiments, the human patient(s) is suffering from post-operative pain. Thus, certain preferred embodiments of the invention are directed to the treatment of post-operative pain, e.g., acute post-operative pain, in a human patient(s) via the intravenous administration of tramadol as described herein.

In certain preferred embodiments, the dose of tramadol administered is an effective dose such as 50 mg, for use in a surgical procedure which is less painful.

In other preferred embodiments, the human patient(s) suffering from pain is unable to ingest an oral dosage form (e.g., of tramadol or another opioid analgesic and/or an NSAID) because the patient is suffering from cancer pain.

The invention is further directed to a method of treating acute pain, comprising administering to a human patient(s) a therapeutically effective dose of tramadol intravenously over the time periods set forth above, and preferably over a time period from about 10 minutes to about 30 minutes such that a reduction in at least one side-effect associated with tramadol therapy is achieved. In certain preferred embodiments, the acute pain is acute post-operative pain. In certain embodiments, the side-effect is nausea, vomiting, or both.

The invention is further directed to a method of treating acute pain, comprising administering to a human patient a therapeutically effective dose of tramadol intravenously over a time period from about 30 minutes to about 48 hours, preferably over a time period from about 24 to about 48 hours in a much slower infusion, e.g., from about 0.05 ml to about 2 ml per minute from a pre-mixed bag containing from about 100 ml to about 3 liters containing an effective amount of tramadol such that a reduction in a side-effect associated with tramadol therapy is achieved. In certain preferred embodiments, the acute pain is acute post-operative pain. In certain embodiments, the side-effect is nausea, vomiting, or both.

Thus, in accordance with the above, the final drug product (containing the intravenous dose of tramadol) may be presented as, e.g., as unit-dose ampoules, unit-dose vials, multi-dose ampoules, multi-dose vials, and drug in pre-mixed bags.

In certain preferred embodiments, the M1 metabolite of tramadol (0-desmethyltramadol) contributes to analgesic effect provided by the present invention (dosage regimen), without being toxic (e.g., without significant side effects) to humans at the administered dose of intravenous tramadol.

The methods of the present invention are described in further detail in the following sections. However, it should be understood that for purposes of the present invention, the following terms have the following meanings:

The term "acute pain" as used herein means pain that has a sudden onset and commonly declines over a short time (days, hours, minutes) and follows injury to the body and which generally disappears when the bodily injury heals.

The term "effective analgesia" is defined for purposes of the present invention as a satisfactory reduction in or elimination of pain, along with the process of a tolerable level of side effects, as determined by the human patient.

The term "effective pain management" means for purposes of the present invention as the objective evaluation of a human patient's response (pain expressed versus side effects) to analgesic treatment by a physician as well as subjective evaluation of therapeutic treatment by the patient undergoing such treatment. The skilled artisan will understand that effective analgesia will vary according to many factors, including individual patient variations.

The term "breakthrough pain" means pain which the patient experiences despite the fact that the patient is being administered generally effective amounts of, e.g., an opioid analgesic such as buprenorphine.

The term "rescue" refers to a dose of an analgesic which is administered to a patient experiencing breakthrough pain.

An "effective amount" is an amount sufficient to effect beneficial or desired clinical results including alleviation or reduction in pain. In some embodiments, the "effective amount" may reduce the pain of ongoing pain and/or breakthrough pain (including ambulatory pain and touch-evoked pain).

The term "parenterally" as used herein includes subcutaneous injections, intravenous, intramuscular, intrasternal injection or infusion techniques.

The term "patient" as used herein refers to a warm blooded animal such as a mammal which is the subject of trauma, e.g., surgical trauma. It is understood that at least humans, dogs, cats, and mice are within the scope of the meaning of the term.

As used herein, the term "treat" or "treatment", or a derivative thereof, contemplates partial or complete inhibition of acute pain, when a composition of the present invention is administered following the onset of acute pain.

DETAILED DESCRIPTION

Figure 1:
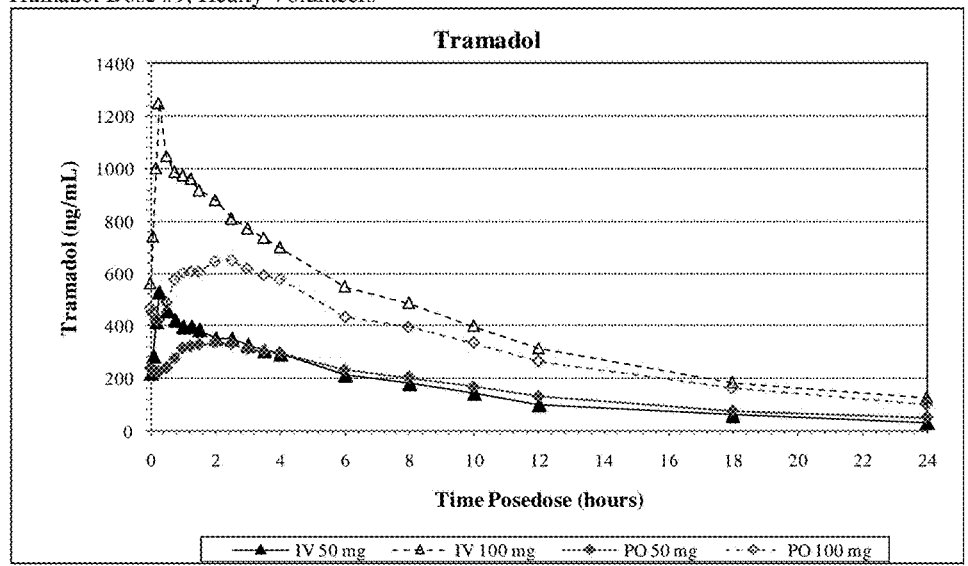
FIG. 1 is a graphical representation of the plasma concentration curve for Treatments A-D after the administration of dose #9 of Example 1.

The chemical name for tramadol is (±)cis-2-[(dimethyl-amino)methyl]-1-(3-methoxyphenyl) cyclohexanol hydrochloride [or (1R,2R)-rel-2-[(dimethyl-amino)methyl]-1-(3-methoxyphenyl) cyclohexanol hydrochloride, (1RS,2RS)-2-[(dimethylamino)methyl]-1-(3-methoxyphenyl) cyclohexanol hydrochloride, (±)-(RR,SS)-2-[(dimethyl-amino)methyl]-1-(3-methoxyphenyl) cyclohexanol hydrochloride]. Unless otherwise specified, the term tramadol refers to the racemic mixture of the (±)cis isomers.

Tramadol is a centrally-acting synthetic analgesic of the aminocyclohexanol group with opioid-like effects. Tramadol is extensively metabolized following administration resulting in a number of enantiomeric metabolites which display different opioid-receptor binding properties, and monoaminergic reuptake inhibition (Grond and Sablotzki, 2004). Both enantiomers of tramadol and (+)-M1 are responsible for the analgesic effect. The primary metabolite [(+)-M1 or (+)-O-desmethyltramadol] of tramadol confers significant μ-opioid activity; (+)-tramadol confers weak μ-opioid activity and significant serotonin reuptake inhibition; and (−)-tramadol is responsible for the inhibition of noradrenaline re-uptake (Gillen et al., 2000; Raffa, 2008). Nonclinical studies have shown that antinociception induced by tramadol is only partially antagonized by the opiate antagonist, naloxone, indicating that non-opioid mechanisms are also involved in its pharmacodynamic action (Collart et al., 1992).

Tramadol has efficacy in management of acute postoperative pain equivalent to morphine and other opioids administered intravenously, although the onset of action for tramadol is slower. The parenteral route has the advantage of immediate bioavailability and faster onset of action than oral, and is available to postoperative patients who cannot take oral medications. Current standard-of-care injectable analgesics (opioids and NSAIDs) have significant adverse effects, including opiate-induced respiratory depression, excessive sedation, hypotension, dependency, increased bleeding risk, renal toxicity and gastrointestinal irritation, which can potentially slow the postoperative rehabilitation process and compound the risk inherent in any surgical procedure.

Tramadol is currently commercially available in various countries/territories in the following forms: 50 mg/ml or 100 mg/2 ml, solution for injection; 50 mg, capsules, hard; 50 mg, prolonged-release tablets; 100 mg, prolonged-release tablets; 150 mg, prolonged-release tablets; 200 mg, prolonged-release tablets; 50 mg, tablets; 100 mg/ml, oral drops, solution; and 100 mg, suppositories. In the U.S., tramadol is approved by the Food and Drug Administration (FDA) and marketed as an oral capsule/tablet for moderate to moderately severe pain in adults, e.g., under the tradename Ultram® (tramadol hydrochloride tablets).

Parenteral tramadol has been used extensively in Europe and other areas of the world for the amelioration of postoperative pain in both adults and children. The efficacy of tramadol has been thoroughly reviewed (Lee C R, McTavish D, Sorkin E M. Tramadol. A preliminary review of its pharmacodynamic and pharmacokinetic properties, and therapeutic potential in acute andchronic pain states. Drugs. 1993; 46:313-340; Scott L J, Perry C M. Tramadol. A review of its use in perioperative pain. Drugs. 2000; 60:139-176; Grond S and Slabotzi A. Clinical pharmacology of tramadol. Clin Pharmacokinet. 2004; 43:879-923). Parenteral tramadol in such territories consists of tramadol 50 mg or 100 mg administered as a slow bolus injection (over 2-3 minutes) every 4-6 hours.

Surgical procedures often result in some form of acute pain. Surgical pain may include nociceptive, neuropathic or psychological components. Nociceptive pain is a pain experienced as a result of nociception, which is detection of a stimulus by a pain receptor (nociceptor) and transmission of the information to the brain along nerves. Nociceptive pain is caused by tissue damage and inflammation in response to trauma. The resulting pain is usually not well localized and is opioid responsive.

Several options are available for postoperative pain management (Singelyn et al., 1998; Sinatra et al., 2002). Options include intermittent "on-demand" analgesia, continuous epidural analgesia with opioids and/or local anesthetics is effective, or to provide a combination of nerve blocks with long-acting local anesthetics and/or opioids initiated intraoperatively and continued into the immediate postoperative period. In the United States (US) and in India, this latter strategy is frequently employed, and most TKA and THA procedures are currently performed with regional (or neuraxial) or other nerve blocks and without general anesthesia. Each of these options for postoperative pain management can be used concomitantly with the intravenous tramadol treatments described herein as recue medicine to treat breakthrough pain.

The present invention is directed in part to tramadol in a pharmaceutically acceptable sterile solution formulation containing an effective dose of tramadol or a pharmaceutically acceptable salt thereof, and a method of administration of the same for the treatment of pain, e.g., postoperatively. Tramadol injection in accordance with the present invention will fulfill an important need by providing a safe and effective alternative injectable analgesic for use in the acute postoperative setting.

Preferably, the dose of tramadol administered in accordance with the present invention is, e.g., from about 50 mg to about 200 mg, and in certain preferred embodiments either 70 mg or 100 mg, provided as tramadol hydrochloride. The tramadol may be provided, e.g., as 50 mg tramadol hydrochloride/1 ml. The injectable tramadol dose is generally intended for in-hospital use, although it can be used in other settings. In certain preferred embodiments, the tramadol is administered intravenously over a time period from about 10 minutes to about 3 hours. In certain preferred embodiments, the therapeutically effective dose of tramadol intravenously over a time period from about 10 minutes to about 45 minutes. Thus, in preferred embodiments, the therapeutically effective dose of tramadol intravenously over a time period from about 10, 11, 12, 13, 14, 15, 16, 17, 18, 19, 20 21, 22, 23, 24, 25, 26, 27, 28, 29 30, 31, 32, 33, 34, 35, 36, 37, 38, 39, 40, 41, 42, 43, 44 or 45 minutes. In preferred embodiments, therapeutically effective dose of tramadol intravenously over a time period from about 10 minutes to about 30 minutes.

In preferred embodiments, the tramadol injection administered in accordance with the present invention is administered as needed for pain relief, from about 50 mg to about 200 mg at suitable therapeutically effective dosing time intervals, e.g., about every 6 hours, up to about 800 mg/day, and preferably not to exceed about 400 mg/day. Further aspects of the invention are directed to diluting the dose of tramadol in from about 50 ml to about 100 ml of a pharmaceutically acceptable fluid for injection (such as normal saline), and standardizing the administration of the injection of the dose of tramadol via the use of a pump. In preferred embodiments, the pump is an infusion pump that is commercially available, such as pumps available from Braun and Hospira.

In other embodiments, the tramadol is administered over a longer time period, e.g., from about 30 minutes to about 24 hours, and in certain embodiments preferably administered over a time period from about 24 to 48 hours in much slower infusion, e.g., from about 0.05 to about 2 ml per minute from a 100 ml-3 liter pre-mixed bag, providing a total tramadol dose over the course of the infusion from about 200 mg to about 800 mg, and preferably up to about 400 mg tramadol over about 24 hours, and from about 200 mg to about 1600 mg tramadol over about 48 hours.

As previously mentioned, the dose of tramadol administered in accordance with the present invention may be diluted in a suitable pharmaceutically acceptable carrier for injection. Examples of such include sterile water for injection, normal saline, etc. Intravenous fluids are well known to those of ordinary skill in the art, and may include other ingredients beyond the dose of tramadol and the carrier/solvent for the tramadol, e.g., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include: alcohol, e.g., 5% alcohol (e.g., in dextrose and water ("D/W") or D/W in normal saline solution ("NSS"), including in 5% dextrose and water ("D5/W"), or D5/W in NSS); synthetic amino acid such as Aminosyn, FreAmine, Travasol, e.g., 3.5 or 7; 8.5; 3.5, 5.5 or 8.5% respectively; ammonium chloride e.g., 2.14%; dextran 40, in NSS e.g., 10% or in D5/W e.g., 10%; dextran 70, in NSS e.g., 6% or in D5/W e.g., 6%; dextrose (glucose, D5/W) e.g., 2.5-50%; dextrose and sodium chloride e.g., 5-20% dextrose and 0.22-0.9% NaCl; lactated Ringer's (Hartmann's) e.g., NaCl 0.6%, KCl 0.03%, $CaCl_2$ 0.02%; lactate 0.3%; mannitol e.g., 5%, optionally in combination with dextrose e.g., 10% or NaCl e.g., 15 or 20%; multiple electrolyte solutions with varying combinations of electrolytes, dextrose, fructose, invert sugar Ringer's e.g., NaCl 0.86%, KCl 0.03%, $CaCl_2$ 0.033%; sodium bicarbonate e.g., 5%; sodium chloride e.g., 0.45, 0.9, 3, or 5%; sodium lactate e.g., ⅙ M; and sterile water for injection The pH of such IV fluids may vary, and will typically be from about 3.5 to about 8 as known in the art.

The dose of tramadol or pharmaceutically acceptable salts thereof can be administered alone or in combination with other medical treatments, or other therapeutic agents, such as NSAIDs. When so-used, other therapeutic agents can be administered before, concurrently (whether in separate dosage forms or in a combined dosage form), or after administration of an active agent of the present invention.

Consistent with the known clinical effects of opioids, nonclinical safety pharmacology studies have shown that tramadol at high doses affects the central nervous system (CNS), producing sedation, impaired mobility, vomiting (dogs), decreased activity, and convulsions (Matthiesen et al., 1998). Also consistent with clinical effects, changes in blood pressure have been observed in cardiovascular studies in rats at high doses (Raimundo et al., 2006). Tramadol use, particularly with high doses, has been associated with seizures, and the risk of seizures is increased in the presence of drugs that reduce seizure threshold, head trauma or prior history of seizures.

The toxicity of tramadol has been summarized by Matthiesen, et al. (1998). The single-dose toxicity of tramadol was similar in all species tested, independent of the route of administration. Notable acute findings included restlessness, unsteady gait, reduced spontaneous activity, exophthalmus, mydriasis, salivation, vomiting (dog), tremor, convulsions, slight cyanosis and dyspnea. The principle findings in repeat-dose toxicity studies in rats and dogs were behavioral/clinical signs and convulsions at doses of ≥25 mg/kg/day. The kidney and liver were identified as potential target organs in rats, with mild effects (minimal tubular vacuolization and perivenular hydropic degeneration, respectively) following repeat intraperitoneal dosing at high doses of tramadol.

There was no evidence of genotoxic potential for tramadol in standard in vitro and in vivo studies (Matthiesen et al., 1998). Carcinogenicity bioassays in mice and rats showed no evidence of carcinogenic potential. An extensive reproductive and teratology program revealed no safety concerns with respect to fertility or teratogenic effects after oral administration (Matthiesen et al., 1998; Yamamoto et al., 1972). Toxicity to offspring only occurred at doses associated with maternal toxicity.

Following oral administration, tramadol is rapidly and almost completely absorbed. The pharmacokinetics of tramadol were evaluated in healthy male volunteers (n=10) in a crossover design using 100 mg PO or IV doses (Lintz et al., 1986). Peak serum concentrations (tmax) were reached approximately 2 hours after oral dosing and the peak serum concentration (Cmax) for PO tramadol was 280±49 ng/mL. The terminal half-life was 5.1 hours for PO and 5.2 hours for IV administration. The area under the serum tramadol concentration-time curve (AUC) was 2488±774 ng·h/mL for PO and 3709±977 ng·h/mL for IV administration. Total clearance was 467±124 mL/min for PO and 710±174 mL/min for IV administration. The absolute bioavailability of the oral dose was 68±13%, based on comparison of the AUC values, while the estimated absorption of the oral dose was 86-88%. The difference between absorption and bioavailability was attributed to first pass metabolism, which was estimated to be ~20%. However, the absolute bioavailability approaches 90-100% with continuous dosing, probably due to saturation of first pass metabolism (Liao et al., 1992). Other studies have corroborated these findings (Grond and Sablotzki, 2004).

The pharmacokinetic profile of tramadol following i.v. and p.o. administration in humans (n=10, male) is summarized in Table 1 below (Lintz W, Barth H, Osterloh O, Schmidt-Bothelt E. Bioavailability of enteral tramadol formulations. 1st communication: capsules. Arzneim Forsch Drug Res. 1986; 36:1278-1283). The absolute oral bioavailability of tramadol was 68% (±13) in humans.

TABLE 1

Pharmacokinetics of Tramadol Following Intravenous and Oral Administration to Humans

| Tramadol (100 mg) | $C_{max}$ (ng/mL) | $t_{1/2}$ (h) | $AUC_{0-24\,h}$ (ng · h/mL) | $V_d$ (L) | CL/F (mL/min) |
|---|---|---|---|---|---|
| i.v. | — | 5.2 ± 0.8 | 3709 ± 977 | 203 ± 40 | 467 ± 124 |
| p.o | 280 ± 49 | 5.1 ± 0.8 | 2488 ± 774 | 306 ± 52 | 710 ± 174 |

Abbreviations: $C_{max}$, maximal concentration; $t_{1/2}$, half-life; AUC, area under the plasma concentration-time curve; CL, clearance; F, bioavailability; $V_d$, volume of distribution The pharmacokinetic profile of tramadol and the (+)-M1 and (−)-M1 metabolites was also evaluated in humans (N=12, male) following p.o. administration of a single 1.5 mg/kg dose of tramadol (Matthiesen, et al., 1993). The data are summarized in Table 2 below:

TABLE 2

Pharmacokinetics of Tramadol and the (+) and (−) Enantiomers of the M1 Metabolite

| Tramadol (1.5 mg/kg, [100 mg]) | $C_{max}$ (ng/mL) | $T_{max}$ (h) | $t_{1/2}$ (h) | AUC (ng · h/mL) | CL/F (mL/min/kg) |
|---|---|---|---|---|---|
| Tramadol | 274 ± 75 | 1.6 ± 0.5 | 5.9 ± 0.7 | 2177 ± 722 | 742 ± 234 |
| (+)-M1 | 147 ± 39 | 1.6 ± 0.5 | 6.0 ± 1.0 | 1258 ± 410 | 642 ± 204 |
| (−)-M1 | 125 ± 32 | 1.5 ± 0.5 | 5.2 ± 0.8 | 908 ± 298 | 883 ± 264 |

Abbreviations: $C_{max}$, maximal concentration; $T_{max}$, time to maximal concentration; AUC, area under the plasma concentration-time curve; CL, clearance; F, bioavailability; $t_{1/2}$, half-life; $V_d$, volume of distribution Tramadol undergoes hepatic metabolism and both the parent drug and the active metabolite are excreted by the kidneys. The active metabolite, M1 (O desmethyltramadol), is produced by the action of CYP2D6 isozyme of the cytochrome P450 enzyme system. It has a half-life of approximately 6.7 hours after oral administration (single dose of 100 mg), compared to a half-life of 5.6 hours for tramadol administered intravenously. Hepatic impairment results in decreased metabolism of both the parent compound and the active metabolite. Tramadol is rapidly distributed after IV administration with a distribution half-life in the initial phase of 0.31±0.17 hours, followed by a slower distribution phase with a half-life of 1.7±0.4 hours (Lintz et al., 1986). The volumes of distribution following PO and IV administration were 306 L and 203 L, respectively, indicating that tramadol has a high tissue affinity. The protein binding of tramadol is approximately 20%; however, saturation of binding sites does not occur in the therapeutic dose range (Ultram® Prescribing Information, 2009).

Elimination half-life increases approximately 2-fold in subjects with renal or hepatic impairment. Patients who metabolize drugs poorly via CYP2D6 (Caucasian population prevalence ~8%) may obtain reduced benefit from tramadol due to reduced formation of M1 (Ultram® Prescribing Information, Ortho-McNeil-Janssen Pharmaceuticals, Inc, 2009).

Studies of IV tramadol in the postoperative setting have shown an acceptable safety profile. Loading doses up to 150 mg IV were not associated with any serious adverse effects (Silvasti et al., 2000). Also, no serious adverse effects were observed in clinical trials of tramadol with mean (±SD) cumulative doses of 449±66 mg (Rud et al., 1994), 677±473 mg (range 128-1750 mg) (Silvasti et al., 2000), and 868.3±412.2 mg (Pang et al., 1999) over 24, 36 and 48 h respectively.

The most common adverse events, nausea, dizziness, headache, somnolence, sweating, fatigue, constipation, dry mouth and vomiting, which are usually mild to moderate in severity and only occasionally lead to premature discontinuation of tramadol.

The Ultram® and Tramal® labels contain several warnings and precautions regarding use of tramadol. The risk of most of these potential adverse events can be minimized by decreasing the dose or excluding use of tramadol in subjects with risk factors associated with these known, rare adverse events. Tramadol metabolism is reduced in the setting of advanced cirrhosis and renal clearance of both tramadol and its metabolites is reduced in individuals with creatinine <30 mL/min. Thus, the dose of tramadol should be reduced by half or the interval doubled in these populations. Dosage adjustment is also recommended in individuals >75 years of age as they have reduced drug clearance. Tramadol is metabolized by CYP2D6 and CYP3A4; thus, drugs that are inhibitors or inducers of these enzymes can alter tramadol metabolism, resulting in decreased efficacy and/or increased risk of seizures or other adverse effects. Tramadol is associated with a low risk for respiratory depression, which is increased in the presence of other opioids, anesthetic agents and other CNS depressants, including alcohol. Respiratory depression due to the opioid activity of tramadol can be reversed with naloxone. Naloxone should be used cautiously as it can potentiate seizures when administered with tramadol. The full range of allergic/hypersensitivity reactions have been reported in association with tramadol administration, including serious and rarely fatal anaphylactoid reactions.

Potentially life-threatening serotonin syndrome may occur with tramadol products with concomitant use of serotonergic drugs such as SSRIs, tricyclic antidepressants, monoamine oxidase inhibitors and triptans.

Tramadol use, particularly with high doses, has been associated with seizures, and the risk of seizures is increased in the presence of drugs that reduce seizure threshold, head trauma or prior history of seizures.

Human studies evaluating the abuse potential of tramadol, administered via IV or PO routes, have also been conducted (Epstein et al., 2006). During the initial dose-ranging studies, seizure was observed following a tramadol dose of 700 mg IV administered over 1 minute and 300 mg IV delivered over 2.5 minutes. No seizures were observed with a tramadol dose of 200 mg IV administered over 5 minutes. The authors hypothesized that toxicity is likely to limit abuse of high doses of IV tramadol. In a subsequent study involving 10 experienced opioid abusers, tramadol (100 and 200 mg IV), morphine (10 and 20 mg IV) and placebo were administered over 5 minutes. The endpoints in the study were subjective; the extent to which subjects "liked" the effects of the drugs, as well as their ability to produce effects common to morphine and benzadrine (assessed by the Addiction Research Center Inventory-Morphine Benzadrine Group [ARCI-MBG] scale). Tramadol and morphine significantly increased ratings of "feel drug effect" compared to placebo. However, neither dose of tramadol increased ratings on the "liking" or ARCI-MBG scale or on any other subjective measure of opiate-like effects. In contrast, morphine 10 and 20 mg doses significantly increased ratings of "liking" and the morphine 20 mg dose increased ratings on the ARCI-MBG scale. Thus, tramadol administered via the parenteral route (IV or IM) is unlikely to be associated with the subjective morphine-like and positive mood effects typical of abuse and addiction.

It is believed that the intravenous dosage regimen of the invention, e.g., as a slow push of a therapeutically effective dose of tramadol contained in a bag over a time period from about 10 to about 45 minutes, preferably from about 15 to about 30 minutes, will provide added safety with respect to the above-mentioned potential adverse events and others, and will provide lower incidence of side effects associated with tramadol administration. It is further believed that the intravenous dosage regimen regimen of the invention where a therapeutically effective dose of tramadol is administered to a human patient(s) over a time period from about 24 hours to 48 hours in much slower infusion will also provide these benefits.

The intravenous tramadol administration as described herein should preferably not be administered for longer than absolutely necessary. If long-term pain treatment with tramadol is necessary in view of the nature and severity of the illness, then careful and regular monitoring should be carried out (if necessary with breaks in treatment) to establish whether and to what extent further treatment is necessary.

The intravenous tramadol formulation in accordance with the invention typically includes tramadol in the form of its hydrochloride salt. However, one of ordinary skill in the art will appreciate that other forms of tramadol may be used, including but not limited to all pharmaceutically acceptable salts of tramadol. Such pharmaceutically acceptable salts may include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

It is contemplated that with respect to the inventive methods for the intravenous administration of tramadol as described herein, other analgesics, preferably opioid analgesics, may be used to treat postoperative pain in the patient(s), as well. It is particularly contemplated that one or more opioid analgesics will be administered post-surgically to the patient as rescue medicine in order to treat breakthrough pain that the patient may experience.

The term "opioid analgesic" refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Opioid analgesics which are useful in the present invention include all opioid agonists or mixed agonist-antagonists, partial agonists, including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, mixtures of any of the foregoing, salts of any of the foregoing, and the like.

In certain preferred embodiments, opioid analgesics include morphine, oxycodone, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof. In certain preferred embodiments, the opioid agonist is morphine. Equianalgesic doses of these opioids are generally known to those persons having ordinary skill in the art.

In certain embodiments, the patient's need for additional analgesic treatment beyond the intravenous tramadol may be ascertained via the use of a surrogate measure of pain. Pain rating scales are used in daily clinical practice to measure pain intensity. The commonly used measurement scales include the Visual Analog Scale (VAS), the Graphic Rating Scale (GRS), the Simple Descriptor Scale (SDS), the Numerical Rating Scale (NRS), and the Faces Rating Scale (FRS). All of these scales have been documented as being valid measures of pain intensity. The three scales most commonly used in the U.S. are the numerical, word and faces scales. One preferred pain rating scale is the visual analog scale (VAS), a 10 cm. vertical or horizontal line with word anchors at the extremes, such as "no pain" on one end and "pain as bad as it could be" at the other. The patient is asked to make a mark along the line to represent pain intensity.

Alternatively, the graphic rating scale (GRS) is a variation of the visual scale which adds words or numbers between the extremes. Wording added might include "no pain", "mild", "severe". The descriptor scale (SDS) is a list of adjectives describing different levels of pain intensity. For example pain intensity may be described as "no pain", "mild", "moderate" or "severe". The numerical pain rating scale (NPRS) refers to a numerical rating of 0 to 10 or 0 to 5 or to a visual scale with both words and numbers. The patient is asked to rate the pain with 0 being no pain and 10 being the worst possible pain. The faces scale was developed for use with children. This scale exists in several variations but relies on a series of facial expressions to convey pain intensity. Grouping patients' rating of pain intensity as measured with a numerical scale ranging from 0 to 10 into categories of mild, moderate, and severe pain is useful for informing treatment decisions, and interpreting study outcomes. In 1995, Serlin and colleagues (Pain, 1995, 277-84) developed a technique to establish the cut points for mild, moderate, and severe pain by grading pain intensity and functional inference. Since then, a number of studies have been conducted to correlate the numerical scales, for example the NPRS, with cutpoints related to levels of pain intensity. Common severity cutpoints are (1 to 4) for mild pain, (5 to 6) for moderate pain, and (7 to 10) for severe pain.

Surrogate measures of opioid efficacy (analgesia) include sedation, respiratory rate and/or pupil size (via pupillometry), and visual analogue scale ("VAS") for "drug effect".

DETAILED DESCRIPTION OF PREFERRED EMBODIMENTS

This invention is further illustrated by the following examples that should not be construed as limiting. Those of skill in the art of pharmaceutical formulation will readily appreciate that certain modifications to the examples may be readily effected. Any methods, materials, or excipients which are not particularly described will be generally known and available those skilled in the drug design and assay and pharmacokinetic analysis.

Example 1

Example 1 is a clinical study in which the primary objective is to compare maximum exposure and cumulative exposures and to establish the comparative bioavailability at steady-state of tramadol 50 mg and 100 mg (Ultram® tablet) administered orally relative to tramadol injection 50 mg and 100 mg administered intravenously in accordance with the invention, and to establish the dose proportionality of tramadol injection at steady state, in healthy adult volunteers. The secondary objectives of the study are to assess the safety and tolerability of the study medication.

The study was an open-label, single-period, randomized, parallel treatment design. The subjects underwent screening within 4 weeks of dosing. A total of 32 subjects were selected for participation. All subjects entered the clinical research unit on Day −1 prior to dosing. A blood sample for pharmacogenomic analysis was obtained at Day 1. This sample was to be used to determine the CYP2D6 phenotype if significant variability among subjects is observed in the pharmacokinetic values. Subjects received study drug every 6 hours beginning on the morning of Day 1 and ending on the morning of Day 3. The first dose on Day 1 and the last dose on Day 3 were administered after a minimum 10 hour fast.

Injectable tramadol was provided in ampoules contain 50 mg of tramadol hydrochloride and sodium acetate as buffering agent in 1 ml of water for injection. The tramadol injection was diluted in 50 ml of normal saline and a pump was used to standardize the administration of the injection. The tramadol injection was administered intravenously over 15 minutes. Tramadol tablets (Ultram®) were administered with 240 ml of water. No food was administered until 4 hours after dosing on Day 3. Standardized meals were provided. Subjects remained confined to the clinical research unit until after completion of the 24 hour post-dose blood sampling and safety assessments (Day 4). Subjects returned to the unit on Day 4 for blood sampling at 36 hours post-dose, and on Day 5 (48 h post-dose) for blood sampling to assess plasma concentrations of tramadol and O-desmethyltramadol. Safety was determined through periodic laboratory tests, medical history, physical examination including vital signs, and monitoring of other medication and supplement usage and adverse events. Study drug tolerability was evaluated by Investigator assessment and evaluation of adverse event frequency and severity, including irritation at the injection site. Subjects who were taking SSRIs, tricyclic antidepressants, antipsychotic agents and MAO inhibitors were excluded from the study.

Each commercially available Ultram® tablet contains 50 mg of tramadol hydrochloride. Inactive ingredients in the tablet are pregelatinized corn starch, modified starch (corn), hypromellose lactose, magnesium stearate, microcrystalline cellulose, polyethylene glycol, polysorbate 80, sodium starch glycolate, titanium dioxide and carnauba wax (Ultram® Full Prescribing Information, 2009).

The treatments were designated A-D: Tramadol for injection (Treatment A—50 mg; Treatment C—100 mg) or Ultram® tablet (Treatment B—50 mg; Treatment D—100 mg) were administered every 6 hours for nine doses, beginning in the morning of Day 1. The tramadol contained in the ampoules (50 mg/1 ml) was diluted in 50 ml of normal saline and a pump will be used to standardize the infusion, to achieve an intravenous administration over 15 (±2) minutes. Tramadol tablets were administered with 240 ml of water. The treatments are defined in Table 3 below. Each subject received only one of the designated treatments.

TABLE 3

| Treatment Group | RVX-109 for Injection (ampoule containing 50 mg/1 mL) | Ultram ® Tablet (50 mg) | Total Amount of Tramadol per Dose |
|---|---|---|---|
| A | 1 | 0 | 50 mg |
| B | 0 | 1 | 50 mg |
| C | 2 | 0 | 100 mg |
| D | 0 | 2 | 100 mg |

The subjects were randomized to receive one of the 4 treatment regimens as outlined above. Subjects were administered Treatments A or C by intravenous administration or Ultram® (Treatment B or D) orally beginning in the morning of Day 1 at approximately 6:00 AM to 8:00 AM. All subjects fasted for at least 10 hours prior to the first dose of study drug. Subsequent doses were administered every 6 hours (±15 min) for a total of 9 doses. Water was allowed ad libitum; however, water was restricted from 1 hour prior to dosing to 1 hour after dosing on Day 3. Following the last dose in the morning of Day 3, no food was allowed until after the 4 hour blood sample had been obtained.

No blinding of study drug was employed in this trial, as the study endpoints were plasma concentrations, which are objective in nature.

Figure 2:
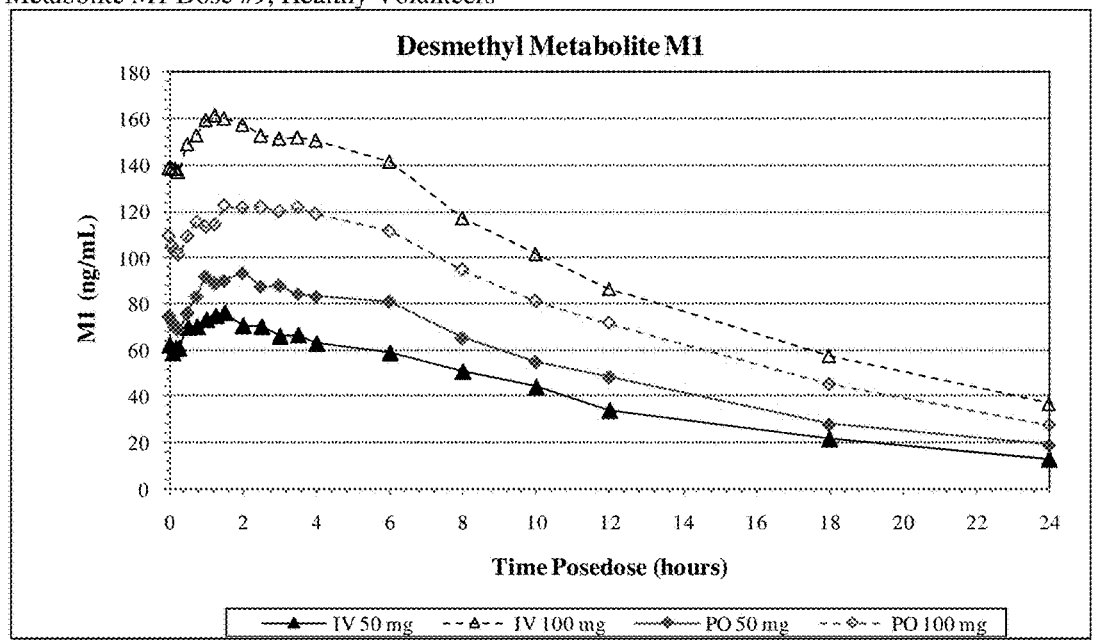
FIG. 2 is a graphical representation of the plasma concentration curve for 0-desmethyltramadol (M1) metabolite of dose #9 of Example 1.

Blood samples for analysis of tramadol and O-desmethyltramadol (M1) plasma concentrations were obtained pre-dose (within 15 min prior to study drug administration) for each dose. On Day 3, blood samples were also collected at 0.083 (5 min), 0.17 (10 min), 0.25, 0.5, 0.75, 1, 1.25, 1.5, 2, 2.5, 3, 3.5, 4, 6, 8, 10, 12, 18, 24, 36 and 48 hours after study drug administration. FIG. 1 is a graphical representation of the plasma concentration curve for Treatments A-D after the administration of dose #9. FIG. 2 is a graphical representation of the plasma concentration curve for O-desmethyltramadol (M1) metabolite. The pharmacokinetic measurements for tramadol obtained from the subjects are set forth in Table 4 below:

TABLE 4

Tramadol PK Parameters in Healthy Volunteers

| $C_{max}$ ng/mL Mean ± SD | $T_{max}$ hours Mean ± SD | $AUC_6$ ng·h/mL Mean ± SD | $AUC_t$ ng·h/mL Mean ± SD | $AUC_\infty$ ng·h/mL Mean ± SD | $\lambda_z$ 1/h Mean ± SD | $T_{1/2}$ h Mean ± SD | $C_{last}$ ng/mL Mean ± SD |
|---|---|---|---|---|---|---|---|
| IV Dose, 50 mg | | | | | | | |
| N = 8 541 ± 126 CV = 23.4% | N = 8 0.375 ± 0.189 CV = 50.4% | N = 8 1965 ± 450 CV = 22.9% | N = 8 4008 ± 1044 CV = 26.0% | N = 8 4035 ± 1057 CV = 26.2% | N = 8 0.105 ± 0.007 CV = 6.2% | N = 8 6.61 ± 0.40 CV = 6.1% | N = 8 2.72 ± 1.40 CV = 51.6% |
| IV Dose, 100 mg | | | | | | | |
| N = 8 1250 ± 236 CV = 18.9% | N = 8 0.406 ± 0.442 CV = 108.8% | N = 8 4733 ± 1240 CV = 26.2% | N = 8 11176 ± 4266 CV = 38.2% | N = 8 11423 ± 4536 CV = 39.7% | N = 8 0.0906 ± 0.0162 CV = 17.8% | N = 8 7.89 ± 1.54 CV = 19.6% | N = 8 18.5 ± 18.8 CV = 101.4% |
| PO Dose, 50 mg | | | | | | | |
| N = 8 355 ± 121 CV = 34.1% | N = 8 1.88 ± 0.78 CV = 41.6% | N = 8 1731 ± 625 CV = 36.1% | N = 8 4362 ± 2026 CV = 46.5% | N = 8 4452 ± 2110 CV = 47.4% | N = 8 0.0979 ± 0.0207 CV = 21.2% | N = 8 7.39 ± 1.72 CV = 23.3% | N = 8 7.36 ± 6.02 CV = 81.8% |
| PO Dose, 100 mg | | | | | | | |
| N = 7 703 ± 210 CV = 29.9% | N = 7 2.32 ± 1.35 CV = 58.2% | N = 7 3365 ± 1009 CV = 30.0% | N = 7 8661 ± 4258 CV = 49.2% | N = 7 8851 ± 4572 CV = 51.7% | N = 7 0.105 ± 0.027 CV = 26.1% | N = 7 7.05 ± 1.97 CV = 28.0% | N = 7 14.1 ± 21.2 CV = 150.3% |

The pharmacokinetic measurements for O-desmethyltramadol (M1) obtained from the subjects are set forth in Table 5 below:

TABLE 5

Desmethyl Metabolite PK Parameters in Healthy Volunteers

| $C_{max}$ ng/mL Mean ± SD | $T_{max}$ Hours Mean ± SD | $AUC_6$ ng·h/mL Mean ± SD | $AUC_t$ ng·h/mL Mean ± SD | $AUC_\infty$ ng·h/mL Mean ± SD | $\lambda_z$ 1/h Mean ± SD | $T_{1/2}$ h Mean ± SD | $C_{last}$ ng/mL Mean ± SD |
|---|---|---|---|---|---|---|---|
| IV Dose, 50 mg | | | | | | | |
| N = 8 78.6 ± 12.4 CV = 15.8% | N = 8 1.53 ± 0.57 CV = 37.5% | N = 8 398 ± 59 CV = 14.8% | N = 8 1086 ± 149 CV = 13.7% | N = 8 1100 ± 149 CV = 13.6% | N = 8 0.0946 ± 0.0083 CV = 8.8% | N = 8 7.37 ± 0.62 CV = 8.4% | N = 8 1.33 ± 0.29 CV = 21.6% |
| IV Dose, 100 mg | | | | | | | |
| N = 8 165 ± 48 CV = 29.0% | N = 8 1.59 ± 1.04 CV = 65.5% | N = 8 904 ± 278 CV = 30.7% | N = 8 2730 ± 1040 CV = 38.1% | N = 8 2839 ± 1188 CV = 41.9% | N = 8 0.0824 ± 0.0190 CV = 23.1% | N = 8 8.91 ± 2.59 CV = 29.0% | N = 8 6.61 ± 7.51 CV = 113.5% |
| PO Dose, 50 mg | | | | | | | |
| N = 8 100 ± 30 CV = 30.0% | N = 8 2.44 ± 1.59 CV = 65.3% | N = 8 508 ± 139 CV = 27.3% | N = 8 1454 ± 401 CV = 27.6% | N = 8 1488 ± 409 CV = 27.5% | N = 8 0.0867 ± 0.0187 CV = 21.6% | N = 8 8.31 ± 1.69 CV = 20.4% | N = 8 2.61 ± 1.56 CV = 59.8% |
| PO Dose, 100 mg | | | | | | | |
| N = 7 130 ± 39 CV = 29.7% | N = 7 2.25 ± 1.15 CV = 50.9% | N = 7 700 ± 223 CV = 31.9% | N = 7 2084 ± 740 CV = 35.5% | N = 7 2124 ± 740 CV = 34.9% | N = 7 0.0971 ± 0.0223 CV = 23.0% | N = 7 7.49 ± 1.83 CV = 24.4% | N = 7 3.40 ± 1.57 CV = 46.4% |

Dose proportionality preliminary analysis obtained from Example 1 is set forth in Table 6 below:

TABLE 6

Dose Proportionality Ratios

| | | $C_{max}$ | $AUC_6$ | $AUC_t$ | $AUC_\infty$ | $T_{1/2}$ | $T_{max}$ |
|---|---|---|---|---|---|---|---|
| Tramadol | IV | 2.33 | 2.39 | 2.69 | 2.72 | 1.18 | 0.917 |
| Tramadol | PO | 1.99 | 1.97 | 1.97 | 1.97 | 0.945 | 1.13 |
| M1 | IV | 2.04 | 2.21 | 2.40 | 2.45 | 1.18 | 0.985 |
| M1 | PO | 1.30 | 1.36 | 1.40 | 1.40 | 0.90 | 0.962 |

The $C_{max}$ and AUC ratios will be approximately 2, if dose proportional. $T_{1/2}$ and $T_{max}$ should have a ratio of approximately 1. The results indicate that the intravenous administration of tramadol is substantially dose proportional for tramadol and M1 metabolite, whereas M1 is not substantially dose proportional orally (PO), which is important because the M1 metabolite contributes to analgesic effect.

The oral bioavailability of the tramadol tablets administered in Example 1 was also calculated. The oral bioavailability was expected to be less than 100%. The results are provided in Table 7 below:

TABLE 7

| | | Bioavailability | | | | | |
|---|---|---|---|---|---|---|---|
| | | $C_{max}$ | $AUC_6$ | $AUC_t$ | $AUC_\infty$ | $\lambda_z$ | $T_{1/2}$ |
| Tramadol | 50 mg | 64.3% | 85.2% | 102.0% | 103.1% | 91.2% | 109.6% |
| Tramadol | 100 mg | 54.9% | 70.3% | 74.8% | 74.6% | 113.6% | 88.0% |
| M1 | 50 mg | 123.6% | 124.7% | 130.5% | 131.8% | 90.1% | 111.0% |
| M1 | 100 mg | 78.7% | 76.9% | 76.2% | 75.4% | 118.2% | 84.6% |

In a totally linear world, the 50 mg and 100 mg doses would have the same oral bioavailability.

In a totally linear world, the various AUC parameters would all give the same number. In a totally linear world, the parent and metabolite would have the same "bioavailability".

Example 2

Example 2 is an open labeled study compared the efficacy of Tramadol 100 mg IV when administered intraoperatively at wound closure, or from first demand of analgesia postoperatively, in patients undergoing Total knee Arthroplasty (TKA) or Total Hip Arthroplasty (THA).

42 patients of both sexes with ages ranges from 29 to 75 years undergoing THA or TKA were included in the study. In the Tramadol on demand group, intravenous morphine was administered to the patient at a dose of 0.05 mg/kg at the end of the surgery. As soon as patient complained of pain in the recovery room, a baseline pain assessment was done using VAS (Visual Analogue Scale), 0 being no pain and 10 being the most excruciating pain. The first dose of IV Tramadol was administered if the pain scale reading was at or above 4. Subsequent doses were repeated every 6 hours for a minimum of 48 hours. Rescue morphine was administered using Patient Controlled Analgesia (PCA). In the other group, tramadol was administered on the table and a bolus of morphine 0.05 mg/ml was administered if the patient asked for analgesia within 6 hours, i.e. before the planned second dose of tramadol. The next dose of tramadol was administered as scheduled after 6 hours and then every 6 hours for 2 days.

The sample size was not based on statistical power, hence for completeness descriptive Statistical Analysis was carried out.

Materials and Methods

The original protocol was for an open label study comparing the efficacy of Tramadol 50 and 100 mg IV in patients undergoing THA/TKA, the use of tramadol intra-operatively or from first demand of analgesia postoperatively and relationship of dosage to BMI. However based on our experiences during implementation, the protocol was amended to assess the efficacy of tramadol 100 mg IV when administered during surgery at wound closure or from first demand of analgesia postoperatively.

The 50 mg group was discontinued when the first patient did not respond and required alternative analgesia. Additional subjects also demonstrated unsatisfactory responses to this regimen. Morphine was used as rescue analgesic in all arms of the study and the quantity of morphine used was the major efficacy parameter.

42 patients of both sexes (24 males and 18 females), from 29 to 75 years, undergoing TKA or THA were included in the study. Subjects met the definition of American Society of Anesthesiologists (ASA) Physical Class 1, 2, or 3, were willing to stay in hospital for a minimum of 48 hours post-surgery and gave informed consent prior to undergoing assessments as per the protocol. Women were either not of child bearing age, or were willing to use methods of contraception during the study period.

Subjects undergoing bilateral TKA or THA, hemiarthroplasty, or revision arthroplasty, those with a history of primary or metastatic bone cancer or Paget's disease were excluded. Also excluded were those with current or historical evidence of any clinically significant disease or condition that might increase the risk of surgery or complicate the subject's postoperative course. Also excluded were those with allergy or hypersensitivity to opioids or tramadol, known physical dependence to opioids or alcohol and those expected to receive gabapentin, pregabalin, ketamine or other peri- or postoperative analgesic adjuncts. Subjects with history of epilepsy, taking anti-epileptics, with depression and suicidal ideation, receiving drugs known to induce or inhibit cytochrome P450 liver enzymes were excluded. Pregnant or breastfeeding women, subjects with cardiopulmonary, hepatic, neurological or renal disease were also excluded. Since this was an open, non-randomized study, the on demand group was completed first followed by Tramadol intraoperative group.

After the patient was transported to the operating room, and I.V. access and monitoring established, subarachnoid block anesthesia (SAB) was administered to the patient. Surgery was commenced after adequate level of block was achieved. In the tramadol on demand group, intravenous morphine was administered to the patient at a dose of 0.05 mg/kg at the end of the surgery. As soon as patient complained of pain in the recovery room, a baseline pain assessment was done using VAS (Visual Analogue Scale), 0 being no pain and 10 being the most excruciating pain. The first dose of IV tramadol was administered if the pain scale reading was at or above 4. Tramadol 100 mg diluted in 100 ml NS was administered over 15-30 min. Subsequent doses were repeated every 6 hours for a minimum of 48 hours.

After the patient received a first dose of IV tramadol, the patient was connected to a PCA pump with morphine (1 mg/ml). PCA was set to deliver a bolus dose of 1 ml with lock out interval of 10 minutes. No background infusion of morphine was given. The patient was instructed to use the PCA rescue only as necessary.

Pain assessment was carried out at 30 min after the first dose and at 1, 2, 3, 4, 5, 6, 9, 12, 18, 24, 36, 42 and 48 hrs post-operatively. Total amount of morphine required by the patient in first 24 hrs of surgery and subsequent 24 to 48 hrs post operatively was recorded.

In the other group, tramadol was administered on the table and a bolus of morphine 0.05 mg/ml was administered if the patient asked for analgesia within 6 hours, i.e. before the planned second dose of tramadol. The PCA was also set up as above to administer morphine in small doses whenever the patient needed rescue medication. The next dose of tramadol was administered as scheduled after 6 hours and then every 6 hours for 2 days.

Adverse events were assessed and recorded throughout 48 hours period. Nausea and or vomiting was treated with ondansetron 100 mcg/kg. Pruritus was treated with 5 mg of diphenhydramine IV if needed.

The sample size was not based on statistical power, as this was a pilot study. The analyses were descriptive. The amount of rescue medication used and the VAS scores at the indicated time points were compared between the groups.

Results

No discernable differences between groups at baseline for demography, vital signs or for distribution of surgeries were noted. Efficacy was measured as the pain intensity difference (PID) at various time points. The results are reported in Table 8 below:

TABLE 8

PAIN Intensity Difference*

| Time in hours post first dose | 1st Dose of Tramadol on demand | | 1st dose of Tramadol at wound closure | |
|---|---|---|---|---|
| | n | Mean score (SD) | n | Mean score (SD) |
| 0.5 | 19 | −0.1 (2.4) | 23 | 0 (0.09) |
| 1 | 19 | −0.5 (2.8) | 23 | −0.3 (1.6) |
| 2 | 19 | 0.2 (2.1) | 23 | −1.2 (1.8) |
| 3 | 19 | 0.3 (2.3) | 23 | −2.2 (1.9) |
| 4 | 19 | 0.3 (2.6) | 23 | −2.6 (2.0) |
| 6 | 19 | 0.1 (2.8) | 23 | −3.2 (2.1) |
| 9 | 19 | 0.8 (2.9) | 23 | −2.7 (2.2) |
| 12 | 18 | 1.4 (2.0) | 23 | −2.2 (2.0) |
| 18 | 18 | 1.2 (2.2) | 23 | −2.2 (2.1) |
| 24 | 18 | 1.6 (1.8) | 22 | −1.9 (1.5) |
| 30 | 17 | 1.9 (2.4) | 22 | −1.6 (1.4) |
| 36 | 17 | 1.9 (2.1) | 22 | −1.3 (1.4) |
| 42 | 17 | 2.1 (2.1) | 22 | −1.7 (1.8) |
| 48 | 17 | 2.4 (2.3) | 22 | −1.4 (1.5) |

*Baseline Score minus Score at each timepoint

The scores show a gradually increasing difference over two days. The two groups could not be compared as the baseline scores in the tramadol at wound closure group was often at 0. This was because patient was asleep and score not recorded. Efficacy was better judged by the use of rescue medication. Given the small sample size, the pain intensity difference was not large enough to be significant (Table 8). A decrease of at least 2 on the VAS score would be considered a clinically significant pain relief, although in this study, the difference was <2 throughout the first day. This could be because the scores were recorded at fixed time points after first dose of tramadol. In the interim, the patient was also receiving rescue medication; hence pain scores were most often <4, the score at which the first dose was given. Due to rescue morphine, the pain is manageable but not nonexistent. On day 2 the differences were approaching 2, again signifying that 100 mg tramadol IV is efficacious in the management of postoperative pain in THA and TKA.

Negative pain difference in the first hour post dosing in the tramadol on demand group indicates that tramadol requires some time to act. This fact is borne out by the pharmacology of the drug. The tramadol metabolite, M1, also has analgesic properties, and this metabolite requires several hours to achieve steady state. The combination of the parent tramadol and the active M1 metabolite is synergistic for pain relief.

The time to first demand of analgesia after surgery was 2.1 (+/−5.4) hours in the tramadol on demand group compared to 2.5 (+/−3) hours in the Tramadol at wound closure group. The results are provided in Table 9 below:

TABLE 9

Time to first demand of rescue medication after the first dose of Tramadol

| | Tramadol on demand | Tramadol at wound Closure |
|---|---|---|
| N | 19 | 22 |
| Mean (hours) | 2.11 | 2.52 |
| SD | 5.37 | 2.97 |

This would indicate that tramadol administered at wound closure was effective for a longer time compared to morphine bolus administered at the same stage of surgery.

The major adverse events were nausea and vomiting, followed by pruritus. Constipation was not reported frequently. This is corroborated by evaluation of concomitant medications, where the number of patients receiving laxatives was not increased after surgery. In addition, the number of patients on anti-emetics and serotonin (5 HT3) antagonists also was not increased. Of note, these medications were often started preoperatively in many cases. The frequency of adverse events did not appear to have a relationship to the body mass index (BMI).

Table 10 below provides the morphine usage in the patients of this study:

TABLE 10

Morphine usage

| | 1st dose Tramadol on demand | | 1st dose Tramadol at wound closure | |
|---|---|---|---|---|
| | N | Mean mg (SD) | N | Mean mg (SD) |
| Loading dose | 19 | 3.69 (0.77) | 23 | 4.05 (0.72) |
| First 24 hours | 19 | 11.03 (8.18) | 22 | 10.57 (5.27) |
| Second 24 hours | 9 | 4 (1.66) | 14 | 3.79 (2.49) |
| In 48 hours | 19 | 12.92 (8.53) | 22 | 12.98 (7.15) |

As can be seen from the results provided in Table 10, while about 11 mg morphine was used during the first 24 hours, only 4 mg was used the next day. The difference is more pronounced if the initial bolus (about 3.5 to 4 mg) is added to the consumption during the first 24 hours. Morphine use reduced over time and was negligible on day 2. As can be seen from the results provided in Table 10, there was no difference between the amount of morphine used in either group, on day 1, day 2 or total. In other words, there was no difference in the use of rescue morphine whether the drug is administered intra-operatively at wound closure or on first demand of analgesic, although the investigator was of the opinion that patient management was easier in the later group.

The total amount of morphine used in both the groups was approximately 15 mg. This amount is considerably less than that used in prior international studies; Leppert W (2009) in a review of tramadol in analgesia for moderate pain has shown that doses as high as 200 mg per day were used in cancer patients. In a study in TKA, by Singleyn F J et al (1998) the amount of morphine used through PCA was 67+/−26 mg. This is again much more than the amount of rescue morphine used in this study.

The results of this study demonstrate that Tramadol 100 mg IV administered four times daily ("QID") is effective in relieving postoperative pain in THA and TKA as seen by the reduced use of rescue medication over two days. The amount of rescue morphine used was same whether tramadol was administered intra-operatively at wound closure or on first demand of analgesic by the patient. The 100 mg QID dose is well tolerated in patients with both high and low BMI. Immediate side effects like nausea were believed to be less prominent because of the novel method of administration.

Example 3

In Example 3, studies were undertaken to evaluate the potential toxicity and toxico-kinetic profile of tramadol and tramadol metabolite M1 in Beagle dogs.

One study was undertaken to evaluate the potential toxicity and determine the toxico-kinetic profile of tramadol metabolite M1 at 0 or 4 mg/kg/dose when administered via a 30-minute intravenous infusion to Beagle dogs as 4 doses per day (approximately 6 hours between doses) for 14 consecutive days and to assess the reversibility, progression, and potential delayed effects of metabolite M1 following a 14-day recovery period.

Under the conditions of this investigation, metabolite M1 was well tolerated at a total daily dose of 16 mg/kg, which was determined to be the no observed adverse effect level (NOAEL). At this dose, the resulting mean Cmax values were 1011 ng/mL and 1096 ng/mL in male and female Beagle dogs, respectively. The mean $AUC_{0-6}$ values were 1172 ng·hr/mL and 1233 ng·hr/mL in male and female Beagle dogs, respectively, resulting in a total daily systemic exposure to metabolite M1 in these dogs of 4688 ng·hr/mL in male and 4932 ng·hr/mL in female Beagle dogs.

Clinical pharmacokinetic data at steady-state generated following 9 doses of 100 mg IV tramadol administered every 6 hours resulted in mean Cmax values of metabolite M1 of 165 ng/mL and a mean $AUC_{0-t}$ of 3616 ng·hr/mL. As such, multiples of human exposure to M1 of approximately 6 times for Cmax and approximately 1.3 times for AUC were achieved in the 14-day toxicology study in dogs. This study supports the safety of metabolite M1 at levels that meet or exceed clinical exposure and support systemic safety in humans.

Based on the observations of convulsions for two Beagle dogs given 54 mg/kg/day during the first 3-4 days of the study and body weight losses at this dose level, the No Observed Adverse Effect Level (NOAEL) was determined to be 26 mg/kg/day (4 times/day, 6.5 mg/kg/dose), which corresponded to a Day 14 tramadol $AUC_{0-6}$ value of 1,209±192 ng·hr/mL (Cmax of 1,277±58.6 ng/mL) and 1,523±197 ng·hr/mL (Cmax of 1,530±139 ng/mL) and M1 $AUC_{0-6}$ value 1.49±0.107 ng·hr/mL (Cmax of 2.16±0.252 ng/mL) and 1.60±0.104 ng·hr/mL (Cmax of 2.36±0.358 ng/mL) for male and female Beagle dogs, respectively.

This data supports the conclusion that tramadol administered to humans at a dose of 400 mg/day (approximately 5-6 mg/kg/day) is not toxic.

CONCLUSION

All patents and publications identified in the above paragraphs are hereby incorporated by reference in their entireties. It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims. All of the patents and publications cited herein are hereby incorporated by reference.

What is claimed is:

1. A method of treating acute post-operative pain, comprising administering to a human patient undergoing an operation a dose of about 50 mg of tramadol at from about 2 to about 6 hour time intervals for at least about 48 hours to treat pain in said patient, wherein each dose of tramadol is administered intravenously over a time period from 10 minutes to 20 minutes, such that the patient is treated for acute postoperative pain, and wherein the dose of tramadol is based on the tramadol hydrochloride salt.

2. The method of claim 1, further comprising diluting the dose of tramadol in normal saline, and standardizing the administration of the injection of the dose of tramadol via the use of a pump.

3. The method of claim 1, further comprising administering a first dose of tramadol to the patient intra-operatively at wound closure, or from first demand of analgesia post-operatively, and administering said further doses of intravenous tramadol for at least two days post-surgery.

4. The method of claim of claim 3, further comprising also administering one or more doses of an intravenous opioid analgesic which is not tramadol as rescue medicine to the patient to treat breakthrough pain.

5. The method of claim 4, wherein the first dose of tramadol is administered on first demand of analgesia post-operatively, further comprising administering a therapeutically effective dose of the intravenous opioid analgesic to the patient at the end of the surgery.

6. The method of claim 4, wherein the first dose of tramadol is administered to the patient intra-operatively at wound closure, further comprising administering a bolus of a therapeutically effective dose of intravenous opioid analgesic which is not tramadol to the patient if the patient requests analgesia before the second dose of tramadol.

7. The method of claim 4, further comprising administering a rescue opioid analgesic using Patient Controlled Analgesia (PCA).

8. The method of claim 4, wherein the treatment of pain in the patient is opioid-sparing over the first 48 hours post-surgery.

9. The method of claim 4, further comprising administering morphine intravenously to the patient at a dose of about 0.05 mg/kg as a bolus at the end of surgery or upon first demand of analgesia post-operatively.

10. The method of claim 1, wherein the dose of tramadol is provided in a pharmaceutically acceptable carrier for injection in a volume from about 50 ml to about 500 ml.

11. The method of claim 1, wherein at least one dose of tramadol is administered over 15 (±2) minutes.

12. The method of claim 1, wherein at least one dose of tramadol is administered over 10 minutes.

13. The method of claim 1, wherein at least one dose of tramadol is administered over 20 minutes.

14. A method of treating moderate to severe acute pain, comprising administering to a human patient a dose of about 50 mg of tramadol intravenously, and administering further doses of tramadol at from about 2 to about 6 hour time intervals for at least about 48 hours to treat pain in said patient, wherein each dose of tramadol is administered intravenously over a time period from 10 minutes to 20 minutes, such that the patient is treated for moderate to severe acute pain, and wherein the dose of tramadol is based on the tramadol hydrochloride salt.

15. The method of claim 14, wherein at least one dose of tramadol is administered over 15 (±2) minutes.

16. The method of claim 14, wherein at least one dose of tramadol is administered over 10 minutes.

17. The method of claim 14, wherein at least one dose of tramadol is administered over 20 minutes.

18. The method of claim 14, wherein the first dose of tramadol is administered to the patient intra-operatively at wound closure, or wherein the first dose of tramadol is administered on first demand of analgesia post-operatively.

19. The method of claim of claim 14, further comprising also administering one or more doses of an intravenous opioid analgesic which is not tramadol as rescue medicine to the patient to treat breakthrough pain.

20. The method of claim 16, wherein human patient has acute post-operative pain.

21. The method of claim 14, further comprising diluting the dose of tramadol in normal saline, and standardizing the administration of the injection of the dose of tramadol via the use of a pump.

22. The method of claim 14, wherein a reduction in a side-effect associated with tramadol therapy selected from nausea, vomiting, or both is achieved.

23. The method of claim 1, wherein a reduction in a side-effect associated with tramadol therapy selected from nausea, vomiting, or both is achieved.

* * * * *